United States Patent
Guttropf et al.

(10) Patent No.: US 9,950,796 B2
(45) Date of Patent: Apr. 24, 2018

(54) SEATING DEVICE

(71) Applicant: RECARO Aircraft Seating GmbH & Co. KG, Schwaebisch Hall (DE)

(72) Inventors: Roland Guttropf, Blaufelden (DE); Cristian Irimia, Schwaebisch Hall (DE); Hubert Krauth, Mainhardt (DE)

(73) Assignee: RECARO Aircraft Seating GmbH & Co. KG, Schwaebisch Hall (DE)

( * ) Notice: Subject to any disclaimer, the term of this patent is extended or adjusted under 35 U.S.C. 154(b) by 29 days.

(21) Appl. No.: 14/782,460

(22) PCT Filed: Apr. 1, 2014

(86) PCT No.: PCT/EP2014/056526
§ 371 (c)(1),
(2) Date: Oct. 5, 2015

(87) PCT Pub. No.: WO2014/161853
PCT Pub. Date: Oct. 9, 2014

(65) Prior Publication Data
US 2016/0039523 A1 Feb. 11, 2016

(30) Foreign Application Priority Data

Apr. 5, 2013 (DE) .................. 10 2013 103 436

(51) Int. Cl.
*B64D 11/06* (2006.01)
*B64D 11/00* (2006.01)

(52) U.S. Cl.
CPC ........ *B64D 11/0636* (2014.12); *B64D 11/003* (2013.01); *B64D 11/0648* (2014.12); *B64D 11/0649* (2014.12); *Y02T 50/46* (2013.01)

(58) Field of Classification Search
CPC ............ B64D 11/0636; B64D 11/0648; B64D 11/003

(Continued)

(56) References Cited

U.S. PATENT DOCUMENTS 2,933,127 A * 4/1960 Brewster ................ B64D 11/06
244/122 R
4,229,040 A * 10/1980 Howell .............. B64D 11/0648
297/232

(Continued)

FOREIGN PATENT DOCUMENTS

DE 10 2004 026 023 A1 12/2005
EP 1 600 376 A2 11/2005

(Continued)

OTHER PUBLICATIONS

Search Report dated Nov. 11, 2013 issued in corresponding DE patent application No. 10 2013 103 436.5 (and partial English Translation).

(Continued)

*Primary Examiner* — David R Dunn
*Assistant Examiner* — Tania Abraham
(74) *Attorney, Agent, or Firm* — Posz Law Group, PLC

(57) ABSTRACT

A seating device with at least one lateral luggage bar, which is provided for being mounted underneath a seat, and with at least one carrier element, which is implemented by a step element and provided for receiving a support force in at least one operating state. In order to achieve improved characteristics regarding complexity and weight, the carrier element and the luggage bar have at least one coupling point, in which the luggage bar and the carrier element are rigidly connected to each other in at least one direction via a form-fit manner, by a substance to substance bond and/or via a force-fit manner and which coupling point is provided for transferring at least a portion of the support force from the carrier element onto the luggage bar.

19 Claims, 3 Drawing Sheets

(58) Field of Classification Search
USPC .............. 297/452.14, 188.08, 452.18, 216.2
See application file for complete search history.

(56) References Cited

U.S. PATENT DOCUMENTS

| | | | | |
|---|---|---|---|---|
| 4,375,300 A * | 3/1983 | Long | ...................... | B60N 2/242 244/122 R |
| 4,489,978 A * | 12/1984 | Brennan | ................. | B60N 2/242 244/118.6 |
| 4,526,421 A * | 7/1985 | Brennan | ................. | B64D 11/06 108/51.3 |
| 4,723,732 A * | 2/1988 | Gorges | ............... | B64D 11/0696 104/165 |
| 4,881,702 A * | 11/1989 | Slettebak | ........... | B64D 11/0693 244/118.6 |
| 5,177,616 A * | 1/1993 | Riday | ................ | B64D 11/0015 248/917 |
| 5,224,755 A * | 7/1993 | Beroth | .................. | B60N 2/242 297/216.1 |
| 5,337,979 A * | 8/1994 | Bales | ................. | B64D 11/0696 244/118.1 |
| 5,553,923 A * | 9/1996 | Bilezikjian | ............ | B64D 11/06 297/232 |
| 5,800,013 A * | 9/1998 | Branham | ................ | B60N 2/242 297/232 |
| 6,578,919 B2 * | 6/2003 | Seibold | .................. | B60N 2/045 296/65.05 |
| 6,588,848 B2 * | 7/2003 | Cheng | ..................... | B60N 2/44 297/423.26 |
| 6,644,738 B2 * | 11/2003 | Williamson | ........... | B60N 2/682 244/122 R |
| 6,669,295 B2 * | 12/2003 | Williamson | ........... | B60N 2/015 297/301.2 |
| 6,672,661 B2 * | 1/2004 | Williamson | ........... | B60N 2/015 297/232 |
| 6,749,266 B2 * | 6/2004 | Williamson | ........... | B64D 11/06 297/248 |
| 6,799,805 B2 * | 10/2004 | Johnson | ............. | B64D 11/0015 244/122 R |
| 7,077,467 B2 * | 7/2006 | Wenzler | ............... | H02G 3/0487 174/481 |
| 7,338,131 B2 * | 3/2008 | Forgatsch | .............. | B64D 11/06 297/188.08 |
| 7,354,019 B2 * | 4/2008 | Bauer | ..................... | A47C 7/74 244/118.6 |
| 7,399,037 B2 * | 7/2008 | Schumacher | .......... | B64D 11/06 297/232 |
| 7,770,966 B2 * | 8/2010 | Johnson | ................ | B60N 3/004 297/122 |
| 8,047,613 B1 * | 11/2011 | Ahad | ..................... | B64D 11/06 297/163 |
| 8,393,680 B2 * | 3/2013 | Zimmermann | .... | B64D 11/0693 297/248 |
| 8,616,631 B2 * | 12/2013 | Westerink | ................ | B60N 2/24 297/188.08 |
| 8,708,410 B2 * | 4/2014 | Scott | ....................... | B64D 11/06 297/234 |
| 8,931,847 B2 * | 1/2015 | Cailleteau | ............ | B60N 2/0224 297/411.3 |
| 9,073,628 B2 * | 7/2015 | Ternoy | .................... | B64C 21/04 |
| 2002/0033622 A1 * | 3/2002 | Jarnail | ................. | B60N 2/4221 297/216.2 |
| 2002/0175554 A1 | 11/2002 | Cheng | | |
| 2005/0264047 A1 | 12/2005 | Bauer | | |
| 2005/0264085 A1 | 12/2005 | Schumacher et al. | | |
| 2006/0006704 A1 * | 1/2006 | Skelly | ...................... | B60N 2/62 297/188.08 |
| 2007/0241233 A1 * | 10/2007 | Cona | ...................... | B64D 11/06 244/118.6 |
| 2008/0106127 A1 * | 5/2008 | Hough | ................... | B64D 11/06 297/188.08 |
| 2012/0086241 A1 | 4/2012 | Ahad | | |
| 2012/0091764 A1 | 4/2012 | Cailleteau et al. | | |
| 2012/0153041 A1 | 6/2012 | Ternoy et al. | | |
| 2013/0038103 A1 | 2/2013 | Scott | | |

FOREIGN PATENT DOCUMENTS

| | | |
|---|---|---|
| EP | 2 465 722 A1 | 6/2012 |
| EP | 2 465 772 A1 | 6/2012 |

OTHER PUBLICATIONS

International Search Report of the International Searching Authority dated Jul. 30, 2014 issued in corresponding International Application No. PCT/EP2014/056526 (and English translation).
Written Opinion of the International Searching Authority dated Jul. 30, 2014 issued in corresponding International Application No. PCT/EP2014/056526 (and English translation).
International Preliminary Report on Patentability dated Oct. 15, 2015 issued in corresponding International Application No. PCT/EP2014/056526 (and English translation).
Chinese Office Action dated Jul. 5, 2016 in the corresponding CN application No. 201480031931.6 (English translation attached.).
Chinese Office Action dated Feb. 27, 2017 for the corresponding CN application No. 201480031931.6(English translation attached).
Chinese Office Action dated May 3, 2017 for the corresponding CN application No. 201480031931.6(English translation attached).

* cited by examiner

SEATING DEVICE

CROSS REFERENCE TO RELATED APPLICATIONS

This application is a U.S. national stage application of International Patent Application No. PCT/EP2014/056526 filed on Apr. 1, 2014 and is based on German Patent Application No. 10 2013 103 436.5 filed on Apr. 5, 2013, the disclosures of which is are incorporated herein by reference.

BACKGROUND

The invention relates to a seating device according to the preamble of patent claim 1.

The objective of the invention is, in particular, to provide a generic device having improved characteristics regarding complexity and weight. The objective is achieved according to the invention by the features of patent claim 1, while advantageous embodiments and further developments of the invention may be gathered from the subclaims.

SUMMARY

The invention is based on a seating device, at least one lateral luggage bar, which is provided for being mounted underneath a seat, and with at least one carrier element, which is implemented by a step element and provided for receiving a support force in at least one operating state.

It is proposed that the carrier element and the luggage bar have at least one coupling point, in which the luggage bar and the carrier element are rigidly connected to each other in at least one direction via a form-fit manner, by a substance-to substance bond and/or via a force-fit manner and which coupling point is provided for transferring at least a portion of the support force from the carrier element onto the luggage bar.

A "luggage bar" is herein to be understood, in particular, as an element which is arranged underneath a seat, in particular underneath an aircraft seat, and is provided for preventing loose elements, e.g. in particular baggage, can pass under the seat and thus, for example, from one seat row into the next one. Herein the luggage bar extends from an underside of the respective seat towards a mounting plane on which the seat is mounted, which means, in the case of an aircraft seat, towards a cabin floor.

A "lateral luggage bar" is herein to be understood, in particular, as a portion of a luggage bar arranged at a side of the seat that faces toward an aisle of a passenger cabin. Herein the complete luggage bar may also extend into other regions underneath the seat and may, for example, extend in a transverse direction of the seat to an opposite side of the seat. "Underneath a seat" is herein to mean, in particular, viewed from a seat bottom of the seat towards a mounting plane on which the seat is mounted. "Provided" is to mean, in particular, specifically designed and/or equipped. By an object being provided for a certain function is to be understood, in particular, that the object fulfills and/or carries out said certain function in at least one application state and/or operating state. By a "carrier element" is to be understood, in this context, in particular a functional element which is provided for a certain function and/or for connecting at least one element, e.g. a lighting element, a holding element, an actuation element and/or another element that is deemed expedient by the person having ordinary skill in the art. Herein "receiving a support force" is to mean, in particular, that the carrier element takes in a force arising from a function of the carrier element, e.g. a weight force, and discharges said force in a non-destructive manner. A "coupling point" is to mean, in particular, a point in which two elements, in particular the luggage bar and the carrier element, are rigidly connected to each other in at least one direction, preferably in at least two directions. The two elements which are connected to each other via the coupling point are herein coupled with each other at least in one direction in a translatory fashion and preferably additionally in a rotary fashion around an axis. The elements may be connected to each other via the coupling point in a form-fit manner, by substance-to substance bond and/or in a force-fit manner. As a result of this, the carrier element can be mounted to a seat, in particular to an aircraft seat, in a particularly easy way, wherein in particular an advantageously low weight of the seating device is achievable and the carrier element can be fastened to the seat by means of an especially advantageously low number of components.

Furthermore it is proposed that the carrier element is implemented by a step element. A "step element" is to be understood, in particular, as an element providing a step region for an individual, in particular providing a step that is elevated with respect to a ground, in particular to the cabin floor, via which an individual may easily and comfortably reach a region that is located farther upwards, e.g. in particular stowage compartments that are arranged above the respective seat. Thus the carrier element can be embodied in a particularly advantageous way and a step opportunity, e.g. in particular the so-called steward step, can be integrated into the seat and fastened to it in a particularly advantageous fashion.

Moreover it is proposed that the carrier element has a substantially L-shaped basic shape. Thereby the carrier element can be implemented, in particular, for being mounted to the seat, in a particularly advantageous fashion.

It is further proposed that the carrier element is provided for being connected to the luggage bar via the coupling point in a form-fit and/or force-fit fashion. Herein "connected in a form-fit and/or force-fit fashion" is to mean, in particular, a releasable connection, a holding force between two structural elements being preferably transferred via a geometrical engagement of the structural elements into each other and/or via a friction force between the structural elements. "In a form-fit fashion" is to mean, in particular, that adjacent surfaces of structural elements that are connected to each other in a form-fit fashion exert a holding force onto each other that acts in a normal direction of the surfaces. In particular, the structural elements are in a geometrical engagement with each other. This allows connecting the carrier element to the luggage bar particularly easily and in a mechanically non-destructive fashion.

It is also proposed that the carrier element comprises a form-fit element, which at least substantially encompasses the luggage bar for the purpose of a form-fit connection. A "form-fit element" is herein to be understood, in particular, as an element which can enter into a form-fit connection via a geometrical engagement with a corresponding form-fit element and/or by lying upon a corresponding form-fit element. In this "at least substantially encompass" is to mean, in particular, that the form-fit element encompasses the luggage bar by at least 50%, preferably by more than 75% and, in an especially advantageous state, completely in one direction. This allows connecting the carrier element to the luggage bar in a particularly simple and advantageous fashion.

Moreover it is proposed that the luggage bar comprises at least one form-fit element, which is implemented corresponding to the form-fit elements of the carrier element. By "being implemented corresponding" is to be understood, in particular, that the form-fit element of the luggage bar is implemented corresponding to the other corresponding form-fit element, as a result of which the two form-fit elements can be connected to each other in a form-fit fashion. This allows connecting the carrier element to the luggage bar by means of the form-fit elements particularly easily.

Furthermore it is proposed that the at least one form-fit element of the luggage bar comprises at least one bump molded to the luggage bar. A "bump molded to" is to be understood, in particular, as a bump that is connected to the luggage bar by substance-to-substance bond and is preferably embodied in a one-part implementation with the luggage bar. Principally it is also conceivable that the form-fit element of the luggage bar, which is embodied corresponding to the form-fit element of the carrier element, is implemented as an element that is embodied separate from the luggage bar, e.g. as a pin that can be introduced into a recess of the luggage bar. Thus the form-fit element of the luggage bar can be embodied in a particularly simple fashion.

It is also proposed that the luggage bar is implemented at least partially by a solid profile. "Implemented at least partially by a solid profile" is herein to mean, in particular, that the luggage bar is implemented by a solid profile by at least 50%, preferably by 80% and in a particularly advantageous embodiment by 100%. As a result of this, the luggage bar can be implemented especially advantageously.

Moreover it is proposed that the luggage bar is embodied at least partially as a flat rod. By a "flat rod" in particular a rod is to be understood that is implemented by a solid profile and has a rectangular cross section, a height of the cross section substantially exceeding a width, preferably being at least double the width. As a result of this, the luggage bar can be implemented by a particularly advantageous solid profile that is embodied in particular space-saving.

It is further proposed that the luggage bar and the carrier element are embodied in a one-part implementation with each other. "In a one-part implementation" is to mean, in particular, at least connected by substance-to-substance bond, e.g. by a welding process, a gluing process, an injection-molding process and/or by another process that is deemed expedient by the person having ordinary skill in the art, and/or advantageously formed in one piece, e.g. by manufacturing from one casting and/or by manufacturing in a one-component or multi-component injection molding process and advantageously from one single cast or blank. The luggage bar and the carrier element can thus be implemented together in an especially advantageous manner, as a result of which, in particular, advantageously a connection of the carrier element to the luggage bar via form-fit elements can be dispensed with. In this case the carrier element and the luggage bar are embodied of a metal in a one-part implementation with each other, preferably of a light-weight metal, e.g. in particular an aluminum. Herein it is also conceivable that the carrier element and the luggage bar embodied in a one-part implementation are implemented by another material that is deemed expedient by the person having ordinary skill in the art, e.g. a plastic, e.g. in particular a fiber-reinforced composite plastic. It is herein also conceivable that the carrier element and the luggage bar are composed of several components and are made of a plurality of different materials that are connected to each other.

The seating device according to the invention is herein not to be restricted to the application form and embodiment described above. In particular, the seating device according to the invention may have, for implementing a functionality herein described, a number of individual elements, structural components and units that differs from a number that has been mentioned herein.

BRIEF DESCRIPTION OF THE DRAWINGS

Further advantages may be gathered from the following description of the drawings. In the drawings two exemplary embodiments of the invention are depicted. The drawings, the description and the claims contain a plurality of features in combination. The person having ordinary skill in the art will purposefully also consider the features separately and will find further expedient combinations.

DETAILED DESCRIPTION

Figure 1:
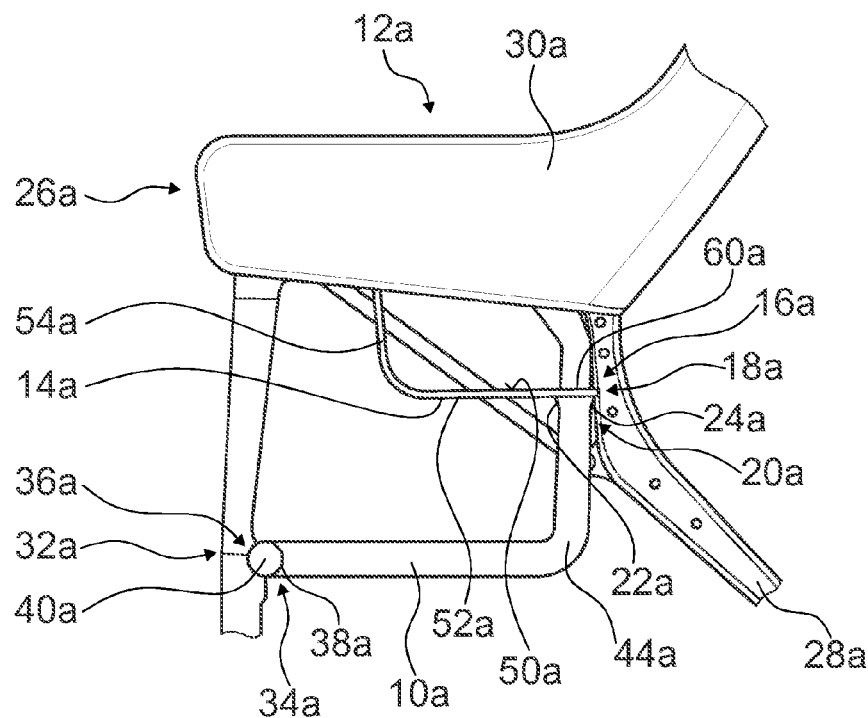
FIG. 1 is a lateral view of a portion of a seat with a seating device according to the invention, in a first exemplary embodiment.
Figure 2:
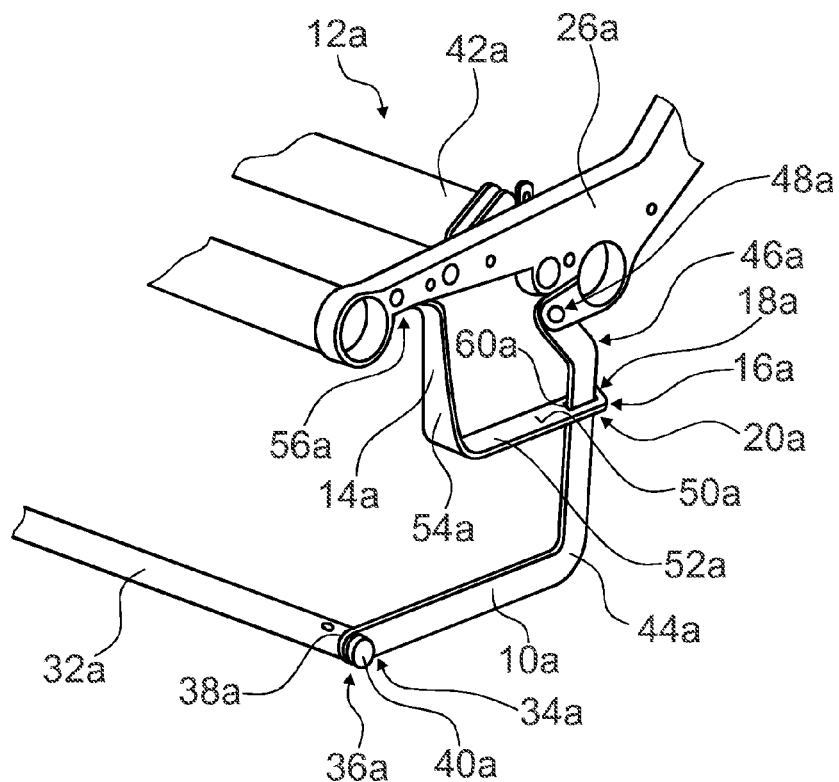
FIG. 2 is a schematic view of the seating device according to the invention.
Figure 3:
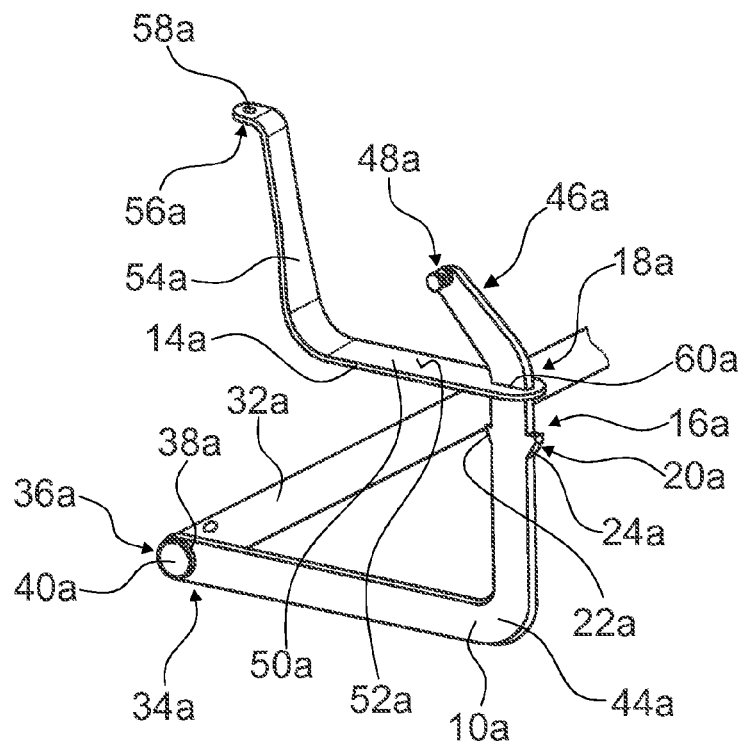
FIG. 3 is a schematic view of the seating device with a luggage bar and with a step element during an assembly.
Figure 4:
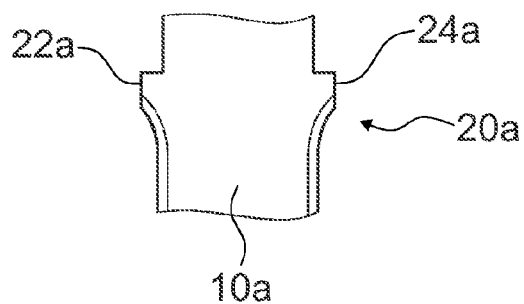
FIG. 4 is a detailed view of a form-fit element of the luggage bar.
Figure 5:
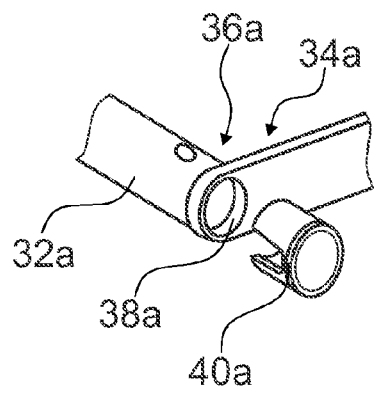
FIG. 5 is a detailed view of a connection of the luggage bar to a front cross bar of the seat.

FIGS. 1 to 5 show a first exemplary embodiment of a seating device according to the invention. The seating device is part of a seat 12a, which is only partially depicted. The seat 12a is implemented as an aircraft seat. The seating device is implemented as an aircraft seating device. The seat 12a, which is implemented as an aircraft seat, comprises a backrest (not shown in detail) for supporting a back of a passenger and a seat bottom (not shown in detail), which forms a seat surface for the passenger. The seat 12a comprises a mounting unit 28a, at which the backrest and the seat bottom are arranged. The seat 12a, which is embodied as an aircraft seat, is moreover mounted on a cabin floor of a passenger cabin by means of the mounting unit 28a. Further the seat 12a comprises, to the side of the seat surfaces, respectively one seat divider 26a, which respectively delimits the individual seats 12a laterally and separates seats 12a of a seat row from each other. The seat divider 26a is herein provided for mounting an armrest for the respective seats which the seat divider 26a delimits laterally. In an assembled state, the seat divider 26a is covered by a cover 30a.

The seating device comprises a lateral luggage bar 10a. The lateral luggage bar 10a is a portion of the seat 12a, which is embodied as an aircraft seat and which abuts an aisle in the passenger cabin with one side. The seat 12a, which is embodied as an aircraft seat, herein comprises further luggage bars, which are not shown in detail and are arranged at other points of the seat 12a. It is herein conceivable that the luggage bars are implemented in the same way as the luggage bar 10a, which is described in the following, while it is principally also conceivable that the other luggage bars, which are not shown in detail, are embodied different from the lateral luggage bar 10a shown. The luggage bar 10a is mounted underneath the seat 12a. The luggage bar 10a is arranged in a region between the seat bottom of the seat 12a and the cabin floor on which the seat 12a, which is embodied as an aircraft seat, is mounted, and thus the luggage bar 10a prevents elements, in particular luggage parts deposited in a foot space of the passenger, from sliding through underneath the seat 12a. The luggage bar 10a herein comprises an L-shaped extension. The seat 12a comprises a front cross bar 32a, which forms a base frame of the seat 12a and is, in an assembled state, arranged near the cabin floor. The front cross bar 32a is also embodied as a luggage bar. The front cross bar 32a has, in an assembled state, a distance from the cabin floor which is less than its distance from the seat bottom of the seat 12a. The luggage bar 10a comprises a front end 34a, which is fixedly connected to the front cross bar 32a via a connection point 36a. Herein it is principally also conceivable that the luggage bar 10a and the cross bar 32a are embodied in a one-part implementation with each other, thus forming together a large luggage bar. The luggage bar 10a comprises a form-fit element 38a, which is embodied as a wall of a pass-through hole by means of which the luggage bar 10a is fixedly connected to the front cross bar 32a. For the purpose of connecting the front end 34a of the luggage bar 10a to the front cross bar 32a, the seating device comprises a separately embodied form-fit element 40a, which is fixedly coupled with the luggage bar 10a via the form-fit element 38a of the luggage bar 10a and is laterally inserted, in a form-fit connection, into the front cross bar 32a, which is implemented as a hollow profile. As a result of this, the luggage bar 10a is fixedly connected to the front cross bar 32a via the form-fit element 40a. Herein it is principally also conceivable that the form-fit element 40a is molded to the luggage bar 10a or the cross bar 32a in one piece. Herein the luggage bar 10a and the cross bar 32a would be connected to each other directly via the form-fit element 40a that has been molded thereto in a one-piece implementation. From the front end 34a the luggage bar 10a extends substantially parallel to the cabin floor towards a rear region of the seat 12a. In a region of a rear support tube 42a of the seat 12a, the luggage bar 10a has a 90-degree deflection and runs from there towards the seat bottom. In a region of a rear end 46a, the luggage bar 10a has a bend towards the front cross bar 32a. The bend has herein an angle of less than 45 degrees. The luggage bar 10a has a pass-through hole at the rear end 46a of the luggage bar 10a. Via the pass-through hole, the luggage bar 10a is connectable to the lateral seat divider 26a of the seat 12a. For this purpose the corresponding seat divider 26a comprises a receptacle, which also has at least one pass-through hole. Via the pass-through hole of the receptacle of the seat divider 26a and the pass-through hole of the rear end 46a of the luggage bar 10a, the rear end 46a of the luggage bar 10a is fixedly connected to the seat divider 26a via a screw connection 48a. The luggage bar 10a is herein implemented by a solid profile. The luggage bar 10a is implemented as a flat rod, having a rectangular cross section. Herein a width of the cross section of the luggage bar 10a is oriented, in an assembled state, parallel to the front cross bar 32a and thus parallel to a transverse direction of the seat 12a. The width of the cross section is herein significantly smaller than a height of the cross section, which latter is in an assembled state implemented parallel to a vertical direction of the seat 12a, which is in particular oriented orthogonally to the transverse direction and to the cabin floor. Herein the luggage bar 10a is manufactured, for example, in a milling process or in a casting procedure. Principally it is also conceivable that the luggage bar 10a has a different cross section and/or a different contour. It is further conceivable that the luggage bar 10a, which is embodied as a flat rod, comprises on one side one or several pockets, which may for example have been milled into the luggage bar 10a. The pockets inserted in the luggage bar 10a may in this case contribute to a reduced weight of the luggage bar 10a. Principally it is herein also conceivable that pockets have been inserted in the luggage bar 10a from several sides. The above description merely serves to describe a possible exemplary embodiment of the luggage bar 10a in detail, but is not to be considered as restricting with respect to the seating device according to the invention.

The seating device comprises a carrier element 14a. The carrier element 14a is provided for receiving a support force in at least one operating state. The carrier element 14a is embodied as a bent flat rod. Herein the carrier element 14a has a cross section the width of which is in an assembled state oriented parallel with respect to the transverse direction of the seat 12a and is significantly larger than a height which extends parallel to a vertical direction of the seat 12a. The carrier element 14a is arranged between the seat divider 26a and the luggage bar 10a. Herein the carrier element 14a and the luggage bar 10a comprise a coupling point 16a, which is provided for transferring at least a portion of the support force from the carrier element 14a onto the luggage bar 10a. A force, in particular a support force, which is introduced into the carrier element 14a during an operating state, is introduced into the luggage bar 10a via the coupling point 16a, and into the seat 12a via the connection of the luggage bar 10a with the base frame of the seat 12a and thereby into the cabin floor, on which the seat 12a is fastened. The carrier element 14a is herein embodied as a step element. The carrier element 14a is embodied as a step element provides a stepping zone 50a, which is elevated with respect to the cabin floor and onto which, for example, a passenger can step for reaching stowage facilities that are arranged above the seat 12a, to have an elevated standing. Principally it is, however, also conceivable that the carrier element 14a is provided for receiving different add-on components, e.g. light elements, holding and/or securing elements. It is, for example, conceivable that the carrier element 14a is provided for fastening light elements which illuminate an aisle of the cabin floor. Principally it is also conceivable that the carrier element 14a is provided for fastening a plurality of different elements. A support force that is herein to be received by the carrier element 14a is in this case implemented by the weight force of the elements connected to the carrier element 14a. Principally it is also conceivable that the carrier element 14a is embodied as a step element and is provided for fastening further elements, e.g. light elements, at the seat 12a.

The carrier element 14a has a substantially L-shaped basic shape. From the coupling point 16a, at which the carrier element 14a is fixedly coupled with the luggage bar 10a, the carrier element 14a runs substantially parallel to a horizontally extending region of the luggage bar 10a towards a front region of the seat 12a, i.e. towards the front cross bar 32a. The horizontally extending region of the carrier element 14a, which starts from the coupling point 16a with the luggage bar 10a, is in the following designated as horizontal region 52a of the carrier element 14a. At an end of the horizontal region 52a of the carrier element 14a that faces away from the coupling point 16a, the carrier element 14a forms a deflection of about 90 degrees, by way of which the horizontal region 52a transforms into a vertical region 54a of the carrier element 14a. The deflection in which the carrier element 14a transforms from the horizontal region 52a into the vertical region 54a is herein embodied as a radius. The vertical region 54a of the carrier element 14a extends in the assembled state away from the cabin floor toward the corresponding seat divider 26a and the seat bottom of the corresponding seat 12a. At an end that faces away from the coupling point 16a, at which the carrier element 14a is coupled with the luggage bar 10a, the carrier element 14a forms a connection region 56a. The connection region 56a is angled with respect to the vertical region 54a of the carrier element 14a and extends parallel to a connection point of the seat divider 26a, to which the carrier element 14a is connected via the connection region 56a. The connection region 56a comprises a pass-through hole 58a, via which the carrier element 14a can be fixedly connected to the seat divider 26a by means of a screw connection. In an assembled state, the carrier element 14a is fixedly connected to the seat divider 26a by means of a screw element through the pass-through hole 58a of the connection region 56a. For this purpose, the seat divider 26a comprises at the connection point an accordingly implemented thread hole, into which the screw element is screwed for fastening the carrier element 14a. Principally it is also conceivable that the carrier element 14a is fixedly connected to the seat divider 26a by means of another fastening element, e.g. by means of a different form-fit element.

The carrier element 14a is connected to the luggage bar 10a via the coupling point 16a in a form-fit fashion. For this purpose the carrier element 14a comprises a form-fit element 18a, which completely encompasses the luggage bar 10a. At the side of the carrier element 14a that faces the luggage bar 10a in an assembled state, the form-fit element 18a is arranged. The form-fit element 18a comprises a pass-through hole 60a, which is embodied corresponding to the cross section of the luggage bar 10a. For this purpose, the pass-through hole 60a has a basic shape that is slightly larger than the cross section of the luggage bar 10a, as a result of which the luggage bar 10a can be guided through the pass-through hole 60a of the form-fit element 18a of the carrier element 14a for mounting the carrier element 14a. In an assembled state the luggage bar 10a is guided through the pass-through hole 60a of the form-fit element 18a of the carrier element 14a, as a result of which the form-fit element 18a of the carrier element 14a completely encompasses the luggage bar 10a.

The luggage bar 10a comprises a form-fit element 20a, which is provided for connecting the carrier element 14a to the luggage bar 10a. The form-fit element 20a is herein embodied corresponding to the form-fit element 18a of the carrier element 14a. The form-fit element 18a of the carrier element 14a and the form-fit element 20a of the luggage bar 10a, via which the carrier element 14a is fixedly connected to the luggage bar 10a, together form the coupling point 16a. The form-fit element 20a forms two bumps 22a, 24a which are molded to the luggage bar 10a. The bumps 22a, 24a molded to the luggage bar 10a are herein arranged at wide sides of the luggage bar 10a, which is embodied as a flat rod, which sides are oriented orthogonally with respect to the transverse direction of the seat 12a. The bumps 22a, 24a of the form-fit element 20a of the luggage bar 10a enlarge the cross section of the luggage bar 10a in the region of the form-fit element 20a, the cross section being then in this region greater than the pass-through hole 60a of the form-fit element 18a of the carrier element 14a. As a result of this, the form-fit element 18a of the carrier element 14a lies, in an assembled state, upon the bumps 22a, 24a of the form-fit element 20a of the luggage bar 10a. The carrier element 14a lies with an underside, which in an assembled state faces the cabin floor, upon support surfaces of the bumps 22a, 24a of the form-fit element 20a of the luggage bar 10a, which support surfaces face away from the cabin floor. Due to the carrier element 14a lying upon the bumps 22a, 24a of the form-fit element 20a of the luggage bar 10a, the carrier element 14a is connected to the luggage bar 10a in a direction of the cabin floor in a form-fit fashion. Principally it is also conceivable that the form-fit element 20a comprises a bump that runs around the luggage bar 10a.

Figure 6:
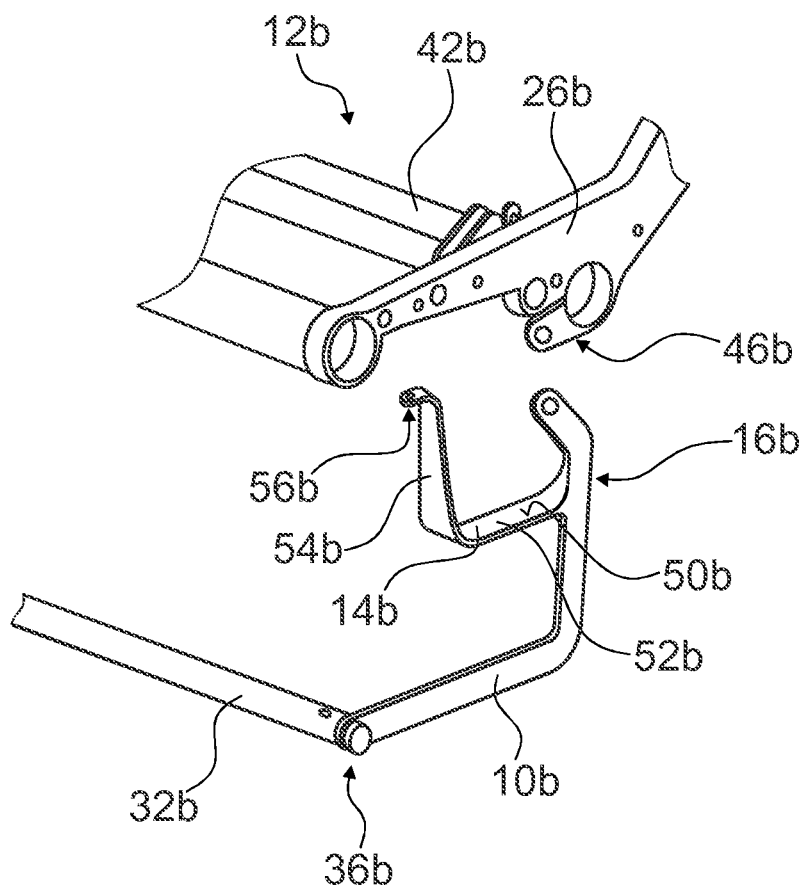
FIG. 6 is a schematic view of a seating device according to the invention, in a second exemplary embodiment.

In FIG. 6 a further exemplary embodiment of the invention is shown. The following descriptions and the drawings are substantially limited to the differences between the exemplary embodiments, wherein regarding structural elements with identical designations, in particular structural elements with the same reference numerals, the drawings and/or description of the other exemplary embodiment, in particular in FIGS. 1 to 5, may be referred to. For distinguishing between the exemplary embodiments the letter a is added to the reference numerals of the exemplary embodiment in FIGS. 1 to 5. In the exemplary embodiment of FIG. 6 the letter a has been replaced by the letter b.

FIG. 6 shows a second exemplary embodiment of a seating device according to the invention. The seating device comprises a lateral luggage bar 10b. The lateral luggage bar 10b is part of a seat 12b implemented as an aircraft seat, which on one side abuts an aisle in the passenger cabin. The seating device comprises a carrier element 14b. The carrier element 14b is provided for receiving a support force in at least one operating state. The carrier element 14b is arranged between a seat divider 26b of the seat 12b and the luggage bar 10b. Herein the carrier element 14b and the luggage bar 10b comprise a coupling point 16b, which is provided for transferring at least a portion of the support force from the carrier element 14b onto the luggage bar 10b. The carrier element 14b is herein embodied as a step element. Differently from the implementation of the first exemplary embodiment of FIGS. 1 to 5, the carrier element 14b and the luggage bar 10b are embodied in a one-part implementation with each other. The carrier element 14b and the luggage bar 10b are implemented by a shared, contiguous structural element. Herein the carrier element 14b and the luggage bar 10b are preferably formed from a blank in one piece, e.g. in a casting process. It is principally also conceivable that the luggage bar 10b and the carrier element 14b are connected by substance-to-substance bond via a welding process or via another process that is deemed expedient by the person having ordinary skill in the art. Principally it is also conceivable that the carrier element 14b is merely connected to the luggage bar 10b. In this case the carrier element 14b would not be connected to the seat divider 26b and an entire support force introduced into the carrier element 14b would be transmitted into the luggage bar 10b via the coupling point 16b.

The invention claimed is:

1. A seating device with at least one lateral luggage bar, which is provided for being mounted underneath a seat and, when installed, the lateral luggage bar is arranged at a side of the seat that is adjacent to an aisle of a passenger cabin, and at least a lower part of the lateral luggage bar extends substantially parallel to the cabin floor towards a rear region of the seat, and the seating device is further provided with at least one carrier element, which is formed separately from the lateral luggage bar and is provided for receiving a support force in at least one operating state, wherein the carrier element and the luggage bar have at least one coupling point, in which the luggage bar and the carrier element are rigidly connected to each other in at least one direction via a form-fit manner, by a substance-to-substance bond or in a force-fit manner and which coupling point is provided for transferring at least a portion of the support force from the carrier element onto the luggage bar, a first end of the carrier element is fixed to an underside of the seat, and a second end of the carrier element is fixed to the luggage bar at the coupling point, and the carrier element is an element providing a step that is elevated with respect to the lower part of the lateral luggage bar.

2. The seating device according to claim 1, wherein the carrier element has a substantially L-shaped basic shape.

3. The seating device according to claim 1, wherein the carrier element is connected to the luggage bar via the coupling point in a form-fit or force-fit fashion.

4. The seating device according to claim 1, wherein the carrier element comprises a form-fit element, which at least substantially encompasses the luggage bar for the purpose of a form-fit connection.

5. The seating device according to claim 4, wherein the luggage bar comprises at least one form-fit element, which is implemented corresponding to the form-fit element of the carrier element.

6. The seating device according to claim 5, wherein the at least one form-fit element of the luggage bar comprises at least one bump molded to the luggage bar.

7. The seating device according to claim 1, wherein the luggage bar is implemented at least partially by a solid profile.

8. The seating device according to claim 1, wherein the luggage bar is embodied at least partially as a flat rod.

9. The seating device according to claim 8, wherein the flat rod is arranged such that a relatively wide surface of the flat rod faces generally upward when the seating device is in an installed position to provide a surface of the step on which a passenger can step.

10. The seating device according to claim 1, comprising a seat divider, wherein the carrier element is arranged between the seat divider and the luggage bar.

11. An aircraft seat, with a seating device according to claim 1.

12. The seating device according to claim 11, wherein the carrier element has a substantially L-shaped basic shape.

13. The seating device according to claim 11, wherein the luggage bar is implemented at least partially by a solid profile.

14. The seating device according to claim 11, comprising a seat divider, wherein the carrier element is arranged between the seat divider and the luggage bar.

15. The seating device according to claim 1, wherein the carrier element comprises a coupling element and the luggage bar comprises a coupling element which is directly connected to the coupling element of the carrier element to form the coupling point.

16. The seating device according to claim 1, wherein the step is generally horizontal when the seating device is in an installed position.

17. A seating device comprising:

a lateral luggage bar, which is mounted underneath a seat, and a carrier element that includes a step, wherein when installed, the lateral luggage bar is arranged at a side of the seat that is adjacent to an aisle of a passenger cabin, and at least a lower part of the lateral luggage bar extends substantially parallel to the cabin floor towards a rear region of the seat, the carrier element is formed separately from the lateral luggage bar, a first end of the carrier element is fixed to an underside of the seat, and a second end of the carrier element is fixed to the luggage bar, the carrier element and the luggage bar are rigidly joined to each other at the second end of the carrier element such that least a portion of the support force from the step is transferred onto the luggage bar, and the step is elevated with respect to the lower part of the luggage bar.

18. The seating device according to claim 17, wherein the carrier element has a substantially L-shaped basic shape.

19. The seating device according to claim 17, wherein a connection between the carrier element and the luggage bar is a form-fit connection or a force-fit connection.

* * * * *